United States Patent [19]

Cha et al.

[11] Patent Number: 5,335,667
[45] Date of Patent: Aug. 9, 1994

[54] METHOD AND APPARATUS FOR DETERMINING BODY COMPOSITION USING BIOELECTRICAL IMPEDANCE

[75] Inventors: Kichul Cha, Somervale, Mass.; Kenneth W. Horch, Salt Lake City, Utah

[73] Assignee: University of Utah Research Foundation, Salt Lake City, Utah

[21] Appl. No.: 979,791

[22] Filed: Nov. 20, 1992

[51] Int. Cl.$^5$ .............................................. A61B 5/05
[52] U.S. Cl. .................................................. 128/734
[58] Field of Search ............... 128/734, 741, 630, 632, 128/693, 774

[56] References Cited

U.S. PATENT DOCUMENTS

| | | |
|---|---|---|
| 3,851,641 | 12/1974 | Toole et al. |
| 3,871,359 | 3/1975 | Pacela |
| 3,971,365 | 7/1976 | Smith |
| 4,116,231 | 9/1978 | Matsuo |
| 4,377,170 | 3/1983 | Carim |
| 4,557,271 | 12/1985 | Stoller et al. |
| 4,793,362 | 12/1988 | Tedner |
| 4,805,621 | 2/1989 | Heinze et al. |
| 4,895,163 | 1/1990 | Libke et al. |
| 4,911,175 | 3/1990 | Shizgal |
| 4,919,145 | 4/1990 | Marriott |
| 4,947,862 | 8/1990 | Kelly |
| 5,063,937 | 11/1991 | Ezenwa et al. |
| 5,086,781 | 2/1992 | Bookspan |

OTHER PUBLICATIONS

Validity of Impedance Predictions at Various Levels of Fatness, Bioelectrical Estimation of Body Composition, by James A. Hodgdon & Patricia I. Fitzgerald, pp. 281-298.

Measurement of body fluid volume change using multisite impedance measurements, Medical & Biological Engineering & Computing, Jan. 1988 pp. 33-36.

Methods for the assessment of human body composition: traditional and new, Am J Clin Nutr 1987; 46:537-56 (1987).

Body Composition Determination in Children Using Bioelectrical Impedence, Growth, Development & Aging, 1988, 52(1), pp. 37-40.

Correlation of whole-body impedance with total body water volume, Journal of Applied Physiology, vol. 27, No. 4, Oct. 1969, pp. 531-534.

Determination of Body Fluid Compartment by Electrical Impedance Measurements, Aviation, Space and Environmental Medicine, Feb., 1975, pp. 152-155.

Assessment of body composition by bioelectrical impedance in a population aged >60y, Am J Clin Nutr 1990; 51:3-6, (1990).

Lean body mass estimation by bioelectrical impedance analysis: a four-site cross-validation study, Am J. Clin Nutr 1988; 47:7-14 (1988).

(List continued on next page.)

*Primary Examiner*—Angela D. Sykes
*Attorney, Agent, or Firm*—Thorpe North Western

[57] ABSTRACT

A method and apparatus for determining body composition of a subject is provided. The composition determinations can include total body fat, lean body mass, total body water, inter-cellular fluid and/or extra-cellular fluid. The subject's body is treated as a plurality of segmented conductors, each of the body segments having a relatively uniform cross-sectional area. By determining the composition of one or more exemplary body segments, the total body composition can be determined. The method in accordance with the present invention selects one or more body segments and introduces a uniform current flow through the body segments. The impedance which each of the body segments presents to the current flow is measured by a pair of voltage sensing electrodes positioned at each end of the body segments. Preferred body segments include the subject's thigh, trunk, and upper arm. The length of the body segment and its cross sectional area are used, as well as the gender of the subject, in combination with the bioelectrical impedance of the body segment to determine the body composition.

28 Claims, 9 Drawing Sheets

OTHER PUBLICATIONS

Body composition by bioelectrical-impedance analysis compared with deuterium dilution and sknfold anthropometry in patients with chronic obstructive pulmonary disease, Am J. Clin Nutr 1991; 53:421–424 (1991).

Estimation of body fluid volumes using tetrapolar bioelectrical Impedance Measurements, Aviation, Space, & Environmental Medicine, Dec. 1988, Henry C. Lukaski, Ph.D. pp. 1163–1169.

Estimation of body composition from bioelectric impedance of body segments, Am J Clin Nutr 1989; 50:221–226 (1980).

Our Committment to Bioelectrical Engineering, The Standard of Impedance Technology, RJL Systems advertisement brochure.

METHOD AND APPARATUS FOR DETERMINING BODY COMPOSITION USING BIOELECTRICAL IMPEDANCE

BACKGROUND

1. The Field of the Invention

This invention relates to apparatus and methods for measuring body composition using bioelectrical impedance analysis (BIA). More particularly, the present invention relates to apparatus and methods for determining body fat, lean body mass, body fluid, and other physiological parameters using bioelectrical impedance analysis.

2. The Prior Art

It is widely recognized that many people can greatly benefit from having a knowledge of their body composition, i.e., what portion of their body comprises fat, lean mass, body fluids, and so forth. For example, athletes need to know their body composition to customize their training regimen. Also, patients can be better treated by a physician if their body composition is known. Furthermore, people who are overweight can benefit from knowing their body composition, especially as they set weight reduction goals.

The importance of body composition is gaining extensive recognition. It is now realized that excess body fat in humans may cause, or at least contribute to, heart attacks, diabetes, hypertension, atherosclerosis, gallbladder disease, osteoarthritis, certain types of cancer, and even premature death. Thus, it is desirable to know what proportion of a person's weight is attributable to fat and other biological components.

The most widely accepted technique for determining what proportion of a person's body mass is attributable to fat is hydrostatic weighing or, in other words, weighing underwater. Since fat, muscle, bone, fluid, and other body components each have a known specific density, hydrostatic weighing allows the proportion of fat in comparison to these other body components to be estimated. While accepted as the "standard" technique for determining total body fat, hydrostatic weighing is also very inconvenient for the subject.

In order to provide more convenient body fat determinations, other techniques have been used. One of the techniques which has been used in the past employs calipers to measure the thickness of one or more skin folds on a body. While the measurement of skin folds is very convenient, it is also inaccurate in many cases. While other techniques have been proposed which are more convenient than hydrostatic weighing, such as isotope dilution, imaging methods, and measurement of fat soluble gases distributed throughout the body, one technique which has received widespread recognition is the measurement of a body's resistance to the flow of electrical current to determine the proportion of fat in the body. More precisely, the measurement of bioelectrical impedance (Z), which includes the electrical parameters of resistance, reactance, and reluctance, is often used to determine the proportion of body fat for a particular subject.

Previously available techniques and apparatus for measuring body fat and other biological components using bioelectrical impedance are exemplified in U.S. Pat. Nos. 4,895,163 and 4,911,175. Such previously available techniques and apparatus generally share several disadvantageous characteristics. Among such characteristics is that the whole body is treated as a single, lumped conductor not accounting for differences in electrical characteristics of each body segment. Also, the previously available techniques and apparatus assume that once the total body impedance is determined, the body composition of all subjects can be obtained by fitting the total body impedance to a predetermined profile. Due to significant differences between individual subjects, however, there is a substantial portion of the population for which the prior techniques provide inaccurate results. In an effort to improve their accuracy, some previously available techniques also consider parameters such as the height, weight, gender, age, and activity level of the subject in addition to the total measured body impedance.

Significantly, while the previous body impedance analysis techniques work for some of the general population, it has generally been unrecognized in the art that the prior techniques do not provide accurate body fat calculations for a significant portion of the population.

In view of the foregoing, it would be a significant advance in the art to provide an improved method and apparatus for measuring body composition by bioelectrical impedance.

BRIEF SUMMARY AND OBJECTS OF THE INVENTION

In view of the above described state of the art, the present invention seeks to realize the following objects and advantages.

It is a primary object of the present invention to provide an improved method and apparatus for measuring body composition by bioelectrical impedance.

It is another object of the present invention to provide a method and apparatus for measuring body composition by bioelectrical impedance which accounts for differences in various subject's bodies.

It is a further object of the present invention to provide a method and apparatus for measuring body composition by bioelectrical impedance which allows body composition for various body segments to be individually measured.

It is yet another object of the present invention to provide a method and apparatus for measuring body composition which is substantially more accurate and more convenient than other methods of determining body composition.

It is a still further object of the present invention to provide a method and apparatus for measuring body composition which produces results which are regularly reproducible.

These and other objects and advantages of the invention will become more fully apparent from the description and claims which follow, or may be learned by the practice of the invention.

The present invention provides a new advantageous method for determining the body composition of a subject. The present invention can provide accurate determinations, which can be expressed as either percent or volume results, of total body fat, lean body mass, total body water, intra-cellular fluid or extra-cellular fluid. The prior methods used in the art assume that the whole body can be treated as a single cylindrical conductor with a uniform cross-sectional area. In contrast to the prior methods, the present invention treats the subject's body as a plurality of segmented conductors, each of the conductors having a relatively uniform cross-sectional area. The present invention can noninvasively and conveniently determine the composition of a particular segment of the subject's body or can use the information obtained from one or more body segments to determine total body composition of the subject.

The method of the present invention includes the steps of selecting one or more body segments with each of the body segments comprising substantially less than the whole body of the subject. A current is injected through each of the body segments. In order to provide uniform current flow through all of the subject's body segments, it is preferred that current be injected into the distal portions of each of the subject's extremities, i.e., adjacent to the subject's hands and feet. In the apparatus of the present invention, a current means for generating a current is provided as well as means for injecting the current into a distal portion of each of the four extremities. Also provided in the apparatus of the present invention is voltage means for measuring voltage and means for sensing the voltages present at the pertinent body segments. A means for outputting the impedance measured for the body segment is also provided. From the voltages sensed, the electrical impedance of the particular body segment can be determined.

Preferably, the impedance of the body segment is determined by positioning a voltage sensing electrode at each end of the pertinent body segment and the difference in the voltage sensed by the pair of electrodes provides the impedance of the body segment in accordance with Ohm's law. Preferred body segments include the subject's thigh, trunk, and upper arm. The length of the body segment and its cross section area (estimated by measuring the circumference of the body segment) may be used, as well as the gender of the subject, in combination with the bioelectrical impedance of the body segment, to determine body composition.

BRIEF DESCRIPTION OF THE DRAWINGS

In order to better appreciate how the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Reference will now be made to the drawings wherein like structures will be provided with like reference designations.

The use of body impedance analysis to estimate body composition is based on the volume conductor theory, which is well known in the pertinent art. Simply stated, the volume conductor theory indicates that the volume of a conductor can be determined by its impedance to current flow. The impedance of a conductor is proportional to, among other things, its length and is inversely proportional to its cross-sectional area as set forth in Equation (1).

$$Z = \zeta * (L/A) \quad (1)$$

where
 Z is impedance;
 $\zeta$ is specific impedance;
 L is conductor length; and
 A is conductor cross-sectional area.

Multiplying the right side of Equation (1) by L/L, and setting A*L equal to the volume of the conductor (V) yields:

$$Z = \zeta * (L*L)/V \quad (2)$$

from which $$V = \zeta * (L*L)/Z \quad (3)$$

Thus, the volume of a conductor can be calculated by measuring the length and the specific impedance of the conductor.

In the case of a human body, most of the current which is injected into the body flows through the fluids contained in the body. Since current flows mainly through the body fluids, total body water is closely related to the conductor volume determined from Equation (3).

Lean body mass (LBM) can be estimated, because lean body mass, which is defined as total body mass minus fat body mass, is proportional to total body water. Once LBM is known, the percent body fat can be calculated in accordance with Equation (4).

$$\% BF = 100 * (Wt-LBM)/Wt \quad (4)$$

where:
 % BF is percent body fat;
 LBM is lean body mass; and
 Wt is body weight.

Figure 1:
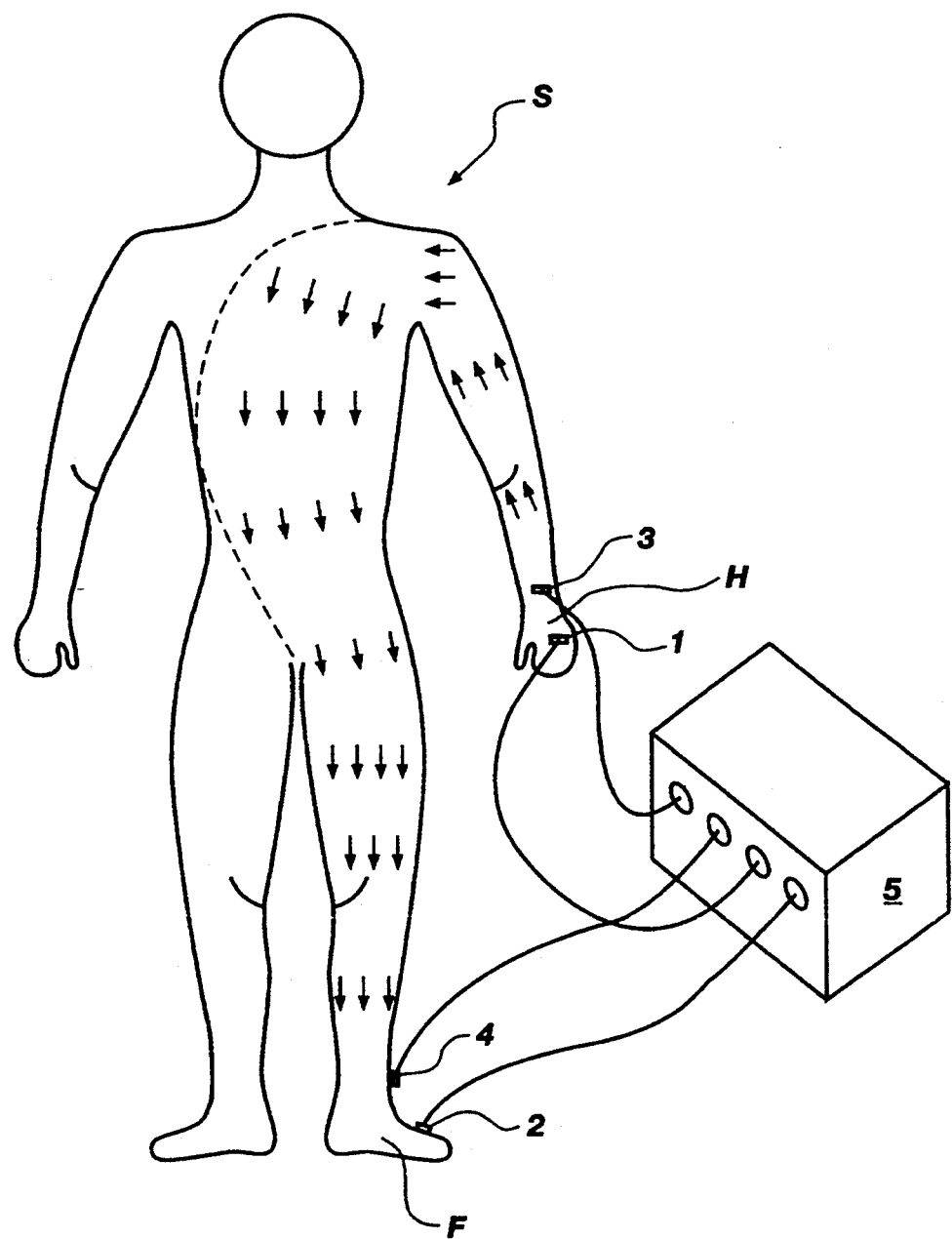
FIG. 1 is a diagrammatic representation of a human subject undergoing a prior art method of determining body composition.

Reference will now be made to FIG. 1 which is a diagrammatic representation of a human subject S undergoing a prior art method of determining body composition. As represented in FIG. 1, to measure impedance of the body as a conductor, a current electrode 1 and a voltage electrode 3 are ipsilaterally placed on the subject's hand H and current electrode 2 and voltage electrode 4 are placed on the subject's foot F. Each of the electrodes is connected to an impedance analyzer 5 as is known in the industry. The electrodes 1 and 2 positioned most distally on the subject's limbs inject a high frequency, low level of current into the subject's body S. The electrodes 3 and 4 positioned more proximally on the subject's limbs are used to measure the resulting voltage drop. In accordance with Ohm's law, the ratio of the voltage to the current gives total body impedance. With the total body impedance having been determined, using prior methods, the length of the subject's body as a conductor is estimated by the height of the subject using empirically gathered information.

By applying equation (3) to the whole body of the subject, the prior body impedance analysis techniques assume that the whole body can be treated as a single cylindrical conductor with a uniform cross-sectional area. For example, a typical prior body impedance analysis equation has the form:

$$LBM = 0.734*(Ht^2/R) + 0.116*Wt + 0.096*X_c + 0.878*Sex - 4.03 \quad (5)$$

where:
LBM is lean body mass;
Ht is height;
R is the resistive component of total body impedance measured between hand and foot;
$X_c$ is the capacitive reactance component of total body impedance measured between hand and foot;
Wt is weight; and
Sex is 0 for females, 1 for males.

Although the accuracy of such prior body impedance analysis improves considerably by adding anthropometric factors such as body shape and body dimensions, the previously used body impedance analysis techniques remain largely an empirical estimation of body composition. Problems with the previous empirical approach include: First, the accuracy of the approach is less than that required for practical applications; Second, the equations used with an empirical approach provide very inaccurate results for subjects who deviate from the norm; Third, previous approaches are not adequate for continuous monitoring of body composition changes for an individual; Fourth, the electrode positions (hand and foot) used in the prior approach are not appropriate for reproducible impedance measurements because distortions in the potential field at these high resistance sites amplify the variations that occur because of inevitable variations in electrode placement; and Fifth, the unilateral current electrode configuration is not suitable for estimation of impedance in the trunk because it introduces a non-uniform distribution of current in this region of the body.

Regarding the unilateral current electrode placement, the arrows shown on the subject represented in FIG. 1 indicate the typical current flow pattern through the subject's body. It will be understood that, even though the arrows are pointing in a single direction, the current generally used is a high frequency alternating current. As shown in FIG. 1, the current flow from the subject's hand to the subject's foot takes substantially the most direct course through the subject's trunk. Thus, the current flow avoids much of the subject's trunk and the subject's opposing arm and leg completely.

In contrast to the prior methods, the present invention does not treat the subject's body as a single cylindrical conductor with a uniform cross-sectional area. Rather, the bioelectrical impedance analysis method for estimating body 4 composition of the present invention treats the subject's body as a plurality of segmented conductors, each of the conductors being chosen so as to have a relatively uniform cross-sectional area.

Figure 2:
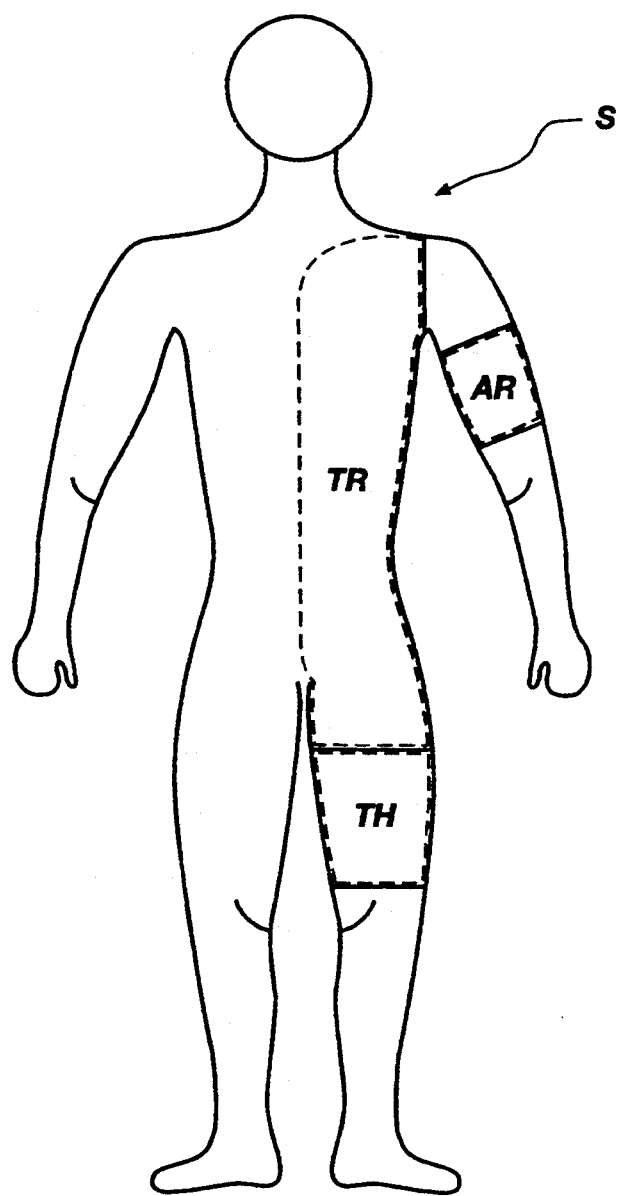
FIG. 2 is a diagrammatic representation of a human subject used to explain one feature of the present invention.

Referring to FIG. 2, exemplary segments of the subject's body are delineated by dotted borders and labeled as TH (on the subject's thigh), TR (on the subject's trunk), and AR (on the subject's upper arm). While not explicitly labeled, each of the segments illustrated on the left side of the subject's body in FIG. 2 has a corresponding segment on the right side of the subject's body.

It will be appreciated that the exact position of these segments will vary from subject to subject and the areas represented in FIG. 2 are intended merely as a guide. Moreover, segments of the subject's body other than those represented in FIG. 2 can also be used. Those segments represented in FIG. 2, however, are preferred for use with the present invention as will be explained in greater detail shortly.

Figure 3A:
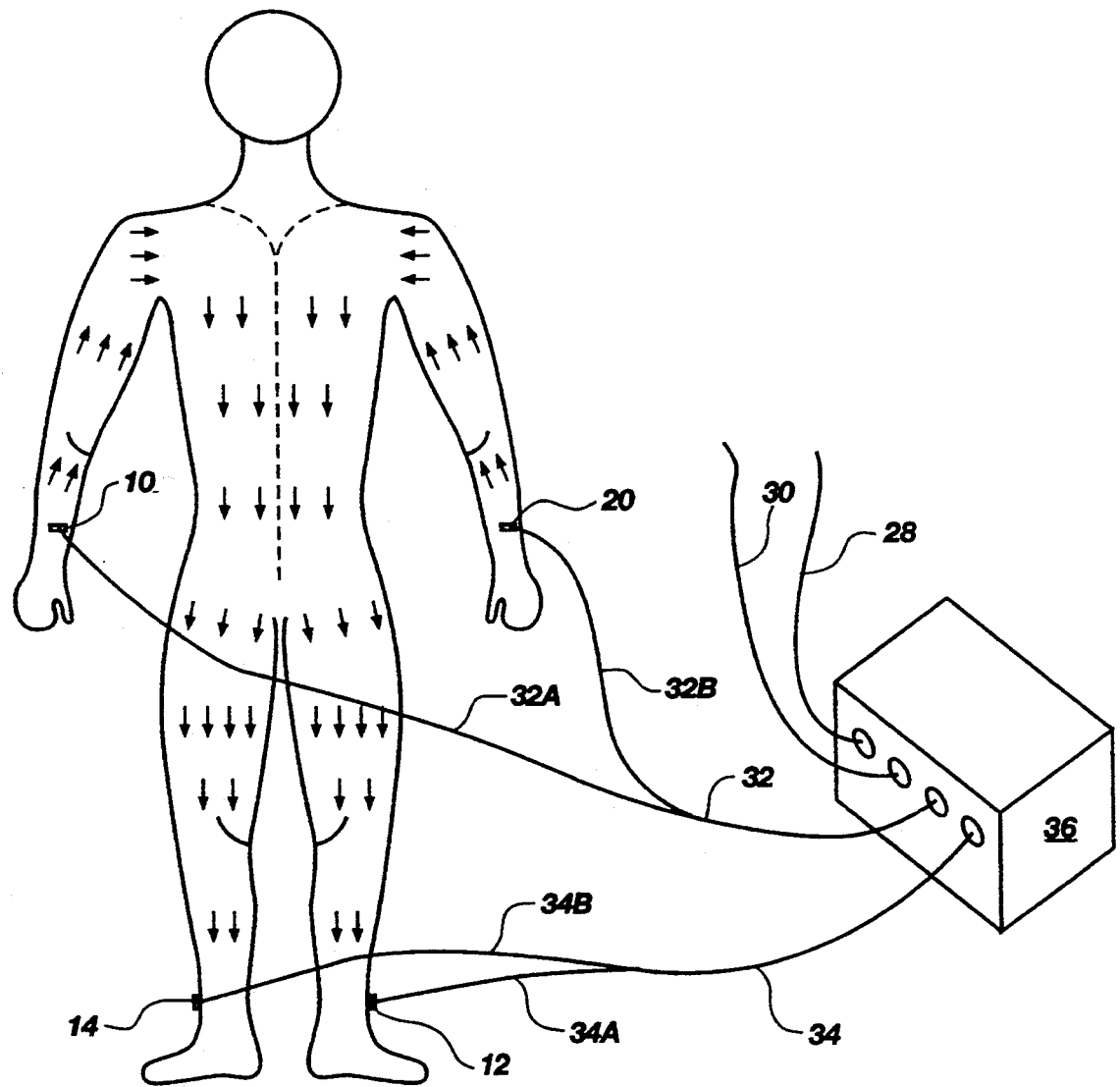
FIGS. 3A–D are diagrammatic representations of a human subject and the apparatus of the present invention being used to determine the subject's body composition.
Figure 3B:
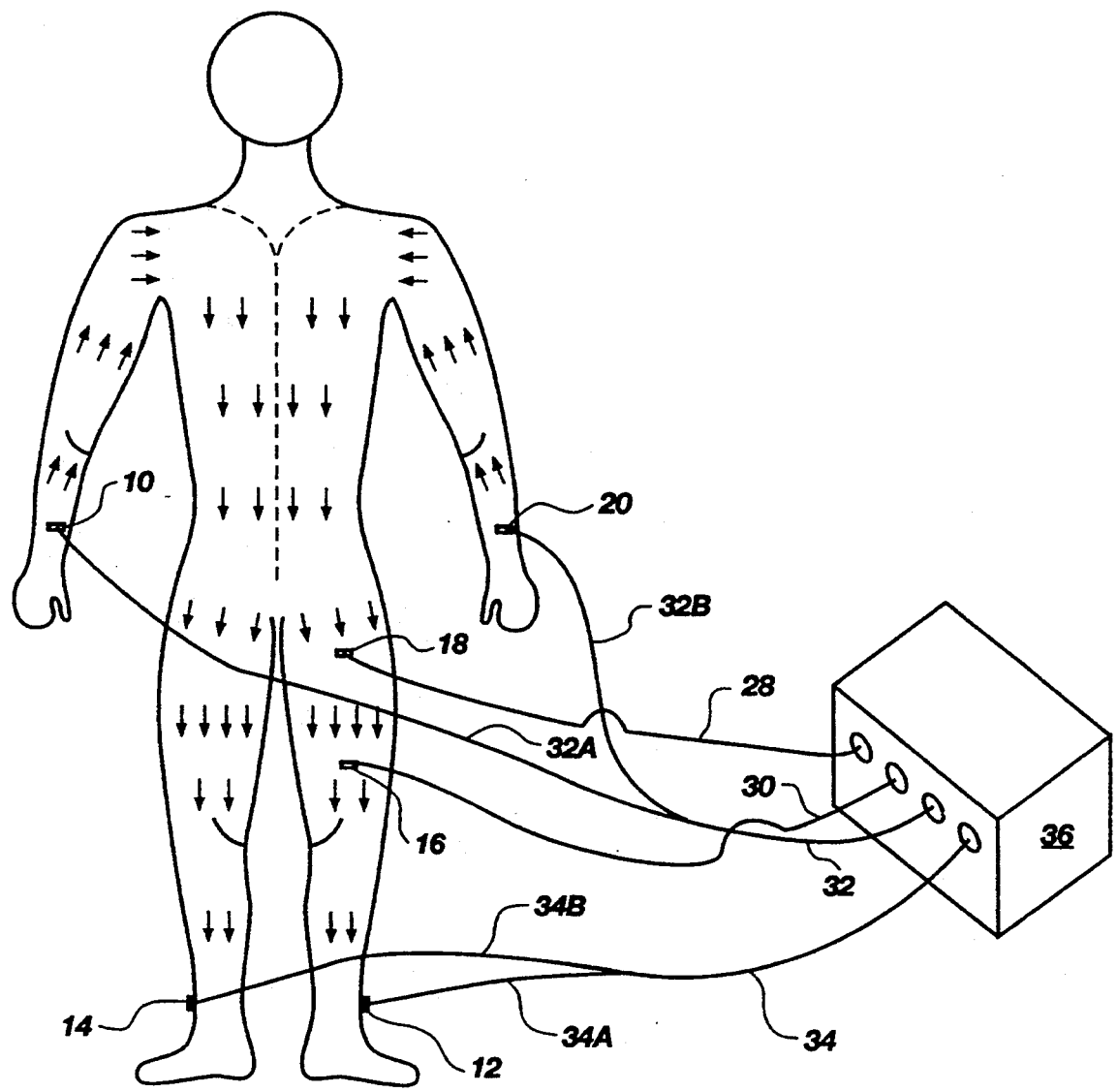
Figure 3C:
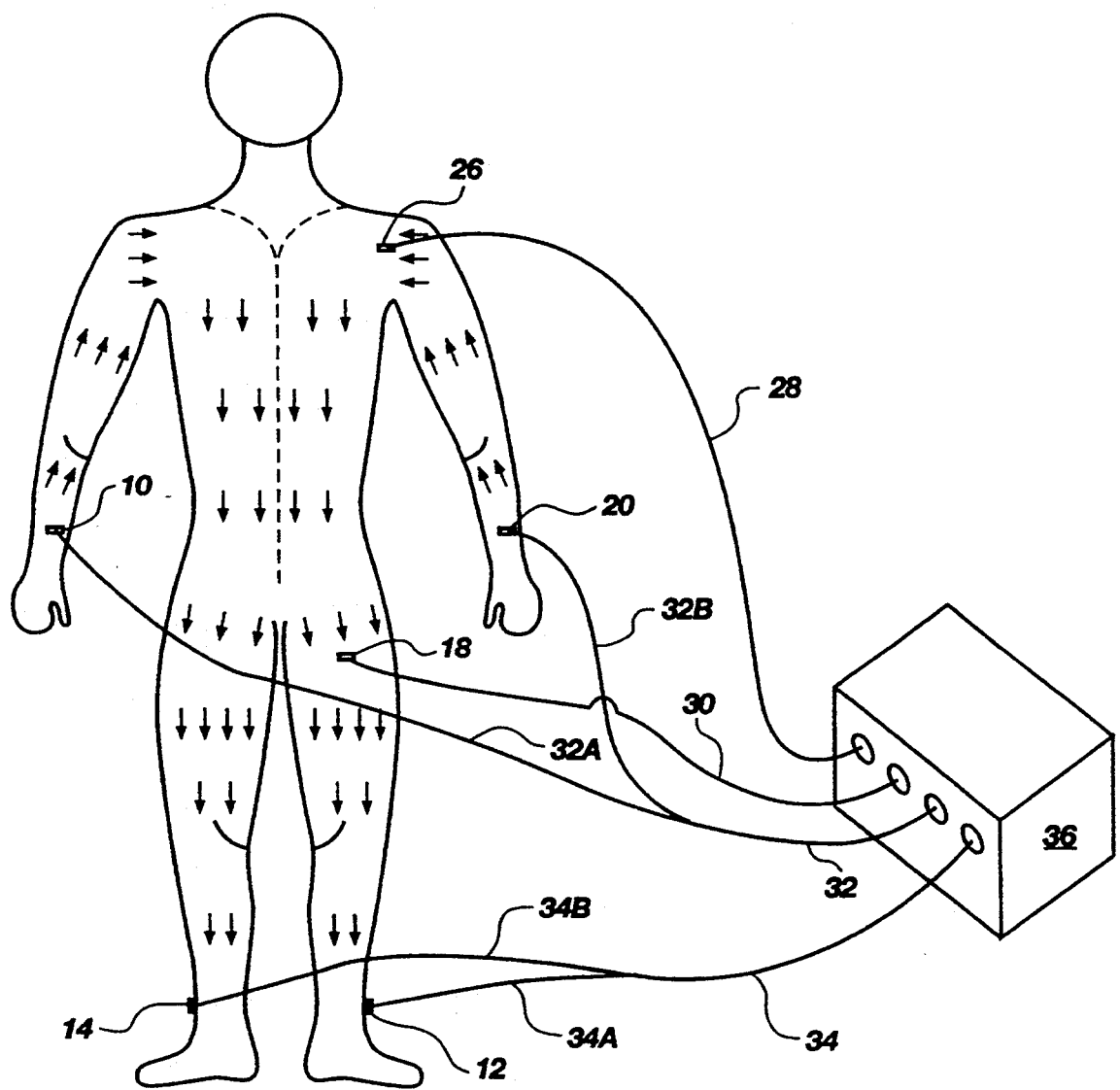
Figure 3D:
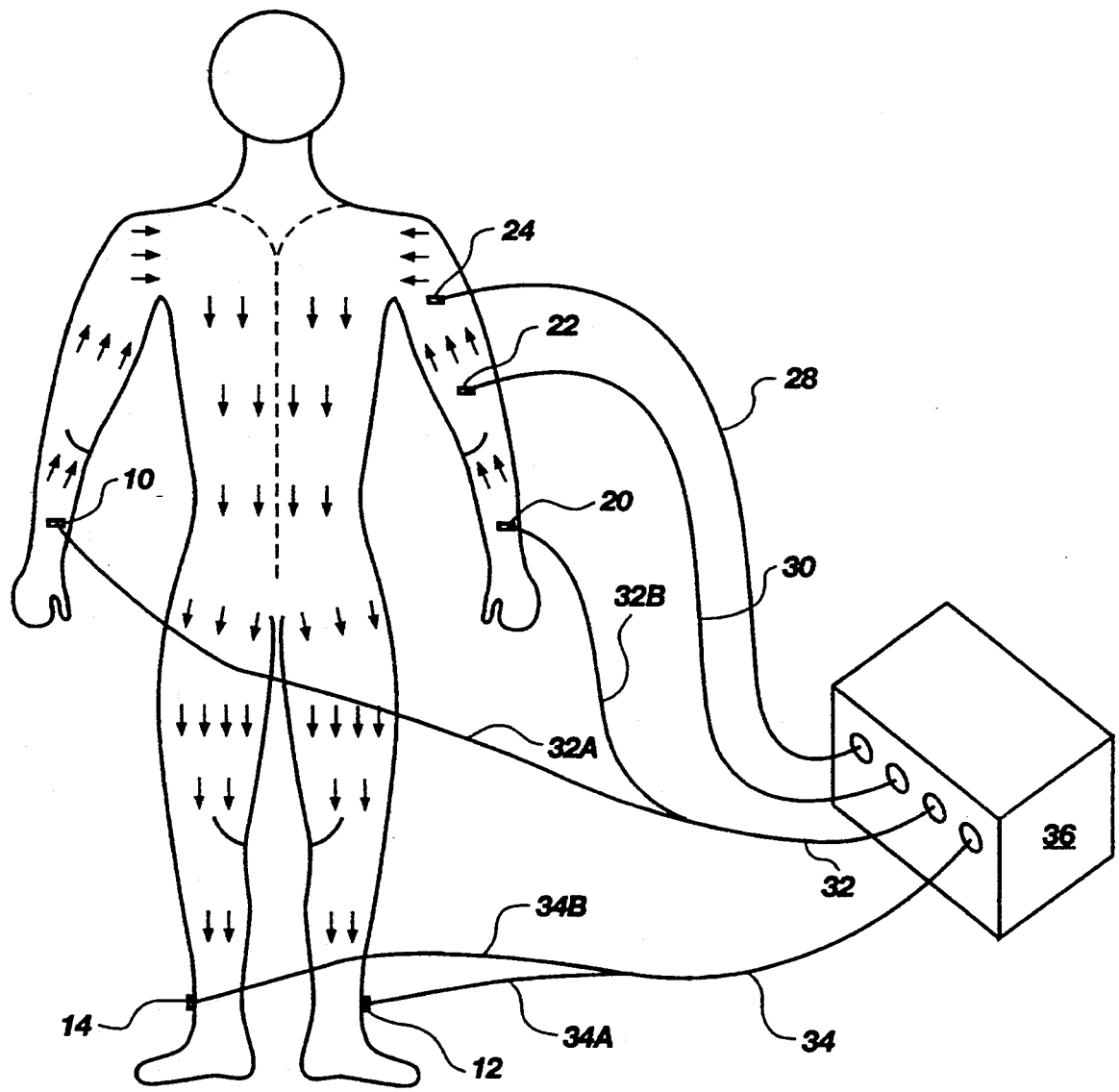

In a great advance over the prior bioelectrical impedance analysis techniques, the present invention treats a plurality of body segments as individual conductors whose impedance is each measured separately. Referring next to FIG. 3A, a portion of the electrode configuration used to carry out the method of the present invention is illustrated. In contrast to prior bioelectrical impedance analysis techniques, current is injected into the subject's body bilaterally using four electrodes which are simultaneously attached to the subject. An additional two electrodes, represented in FIGS. 3B-D, are used to measure impedance of specific body segments as will be explained in connection with FIGS. 3B-D. It will be appreciated that the term "injected," when applied to an electrical current, refers to inducing, communicating, or otherwise causing a current in the subject's body regardless of whether electrons are entering or leaving the subject's body.

In the present invention the electrodes which are used should provide a low resistance electrical connection to the subject's body. It is preferred that commercially available electrodes, such as those generally used when obtaining EKG measurements, be used at least to measure the voltage sensed on the subject's body. Such electrodes provide a low impedance and stable interface to the subject's body. While the prior bioelectrical analysis techniques hardly considered the particulars of the electrodes used, the present invention recognizes that in order to provide the most accurate estimation of body composition, the measured body impedance must be influenced as little as possible by extraneous signals such as those introduced by poor electrical connections to the subject's body.

As represented in FIG. 3A, four electrodes 10, 12, 14, and 20 are current-injecting electrodes placed at locations distally on the subject's arms (adjacent to the subject's hands using electrodes 10 and 20) and distally on the subject's legs (adjacent to the subject's feet using electrodes 12 and 14). As indicated by the arrows superimposed on the subject in FIGS. 3A-D, the current flow which results using this arrangement of the present invention is much more even and encompasses the pertinent portions of the subject's body much better than the prior bioelectrical impedance analysis techniques.

The electrodes 10, 12, 14, and 20 are connected to an impedance analyzer 36 as is available in the industry, for example one available from RJL Systems of Detroit, Mich.. It will be understood, however, that it is within the scope of the present invention to use other devices and that the greatest advantage of the present invention will accrue if a very sensitive and accurate voltage sensing apparatus is used. It is preferred that the electrodes 10, 12, 14, and 20 be connected to the impedance analyzer 36 via leads 32 and 34 which each branch into two parallel leads 32A&B and 34A&B, respectively.

As represented in FIG. 3A, substantially half of the injected current passes through the right side of the body: right arm, right half of the trunk, and right leg as shown by the arrows generally indicating current flow though the subject's body. Also as generally indicated by the arrows, about half of the current passes through the left side of the body. Thus, a relatively uniform distribution of the electrical potential is generated, including in the trunk. A series of conductors, consisting of half of the trunk, the thigh, and the upper arm, is used in accordance with the present invention as the conductor model, with each segment having a relatively uniform cross-sectional area and current distribution.

With the current injecting electrodes 10, 12, 14, and 20 in place, the impedance magnitude (measured as the ratio of voltage to current, ignoring phase shift) is determined for one or more of the body segments. In order to measure the impedance of each body segment, an additional two electrodes are attached to the body segment of interest. Thus, a total of at least six electrodes are simultaneously attached to the subject, in contrast to four electrodes with prior techniques, in order to provide the benefits of even current flow distribution through the subject.

With a current flow through the subject's body established by the current injecting electrodes 10, 12, 14, and 20, the impedance of each body segment is measured by placing a voltage-sensing electrode at each end of the body segment of interest. While each of the body segments are shown as being measured separately, it is within the scope of the present invention to utilize an apparatus which allows simultaneously measuring of the impedance of two or more body segments. It will be appreciated that simultaneously measuring the impedance of two or three body segments by use of eight or ten electrodes and an appropriately designed impedance analyzer would speed up the complete body composition determination.

Referring now to FIG. 3B, for the thigh segment (labeled TH in FIG. 2), a first electrode 12 is placed at a location substantially above the knee joint as represented in FIG. 3B and a second electrode 18 is placed at a location on the upper thigh and below the hip. The impedance of the thigh segment (TH) is determined using the impedance analyzer 36. It will be appreciated that the techniques of the present invention can be carried out on either side of the subject's body or on both sides of the subject's body simultaneously.

Referring next to FIG. 3C, for the trunk segment (labeled TR in FIG. 2) the electrode 18 is placed as described above and electrode 26 is placed at a location on the upper torso adjacent to the subject's shoulder. The impedance of the trunk segment (TR) is then determined using the impedance analyzer 36. When measuring the impedance of the body segments, pairs of electrodes can be placed on one or both sides of a subject's body as well as multiple pairs of electrodes being simultaneously placed at a number of different segments on the subject's body.

Referring next to FIG. 3D, for the arm segment (labeled AR in FIG. 2) a distal electrode 22 is placed at a location slightly above the elbow joint as represented in FIG. 3D and a proximal electrode 24 is placed at a location substantially on the upper arm and below the shoulder joint. The impedance of the arm segment (AR) is then determined using the impedance analyzer 36.

The measured voltage difference between the pairs of electrodes is used to determine the impedance of each of these segments of the subject's body.

When any of the before mentioned body segments are used, or any other body segments are used, the positioning of the voltage sensing electrodes should be made with care. For example, it is preferred that the voltage electrodes be maintained a distance from any of the current injecting electrodes which is at least equal to the diameter of the body segment upon which the electrode is positioned.

It will be appreciated that each of the body segments TH, TR, and AR is preferably considered separately and the composition of each body segment can be separately determined. In this way, the characteristics of each of the body segments can be individually determined and anthropomorphic and physiological differences between subjects taken into account.

In accordance with one aspect of the present invention, the dimensions of each body segment whose impedance is to be measured should be carefully obtained. Each of the segments are preferably measured for length, i.e., the distance between electrodes, and the circumference around the body segment.

Figure 4:
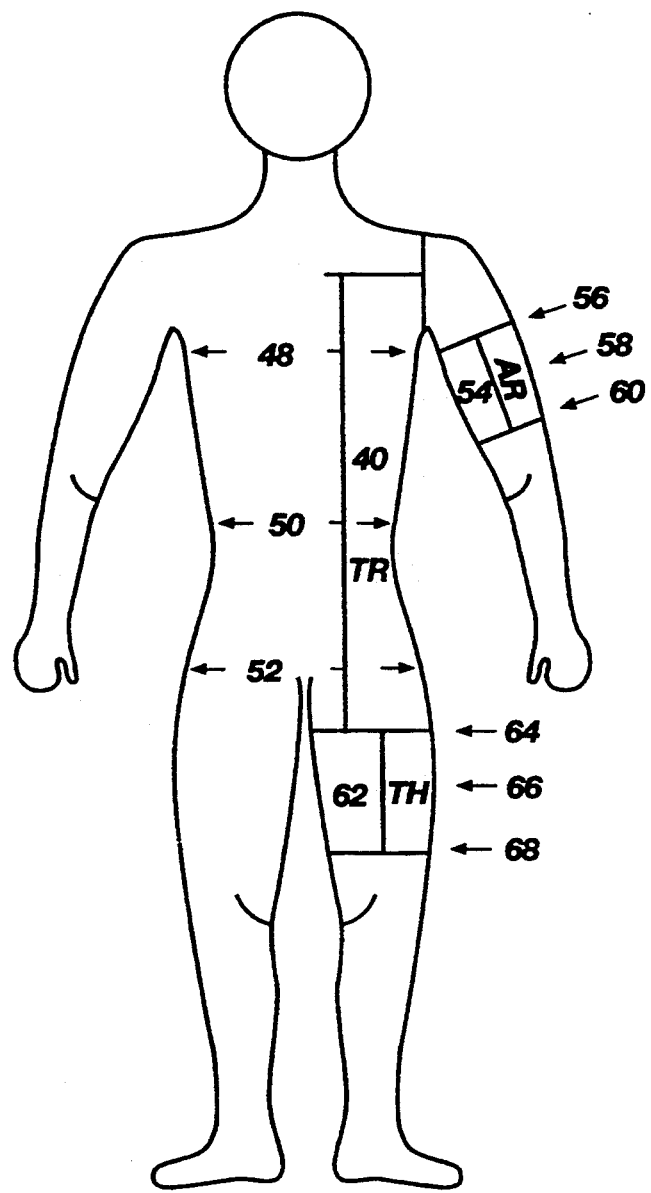
FIG. 4 is a diagrammatic representation of a human subject used to further explain the method of the present invention.

The length of the conductor in each segment is determined by the distance between the corresponding pair of voltage electrodes, as shown in FIG. 4, for the thigh TH, the trunk TR, and the upper arm AR. The average cross-sectional area of the conductor is preferably calculated from a plurality of circumference measurements as will be explained shortly.

In order to increase the accuracy of the present invention, it is preferred that several circumferential measurements of each body segment be obtained. Referring now to FIG. 4, for the thigh segment (TH), the length of the segment, indicated at 62, between the electrodes is measured. The circumferences at each end of the thigh segment (TH), indicated at 64 and 68, and at the approximate midpoint of the thigh segment, indicated at 66, also are each measured.

Still referring to FIG. 4, for the trunk segment (TR), the length of the segment, indicated at 40, is measured. The circumferences of the trunk segment (TR) are measured at the chest (indicated at 48), waist (indicated at 50), hip (indicated at 52), and at the upper thigh (indicated at 64).

In the case of the arm segment (AR), the length of the segment, indicated at 54, is measured. Circumferences of the arm segment (AR) are also measured at both ends of the segment (indicated at 56 and 60) and at the approximate midpoint of the arm segment (indicated at 58).

Once obtained, the segment length and circumference measurements are used to calculate an average cross-sectional area for each of the segments. It will be appreciated that the positions indicated in FIG. 4 are merely exemplary and other positions may be used or additional positions may be used to obtain measurement of the body segments. The measurements indicated in FIG. 4 are presently preferred and, while additional or different measurements can be used, they provide the advantageous results of the present invention.

Having obtained the measurements of each of the body segments and having measured the bioelectrical impedance of each of the segments, the method of the present invention utilizes a number of the gathered variables to arrive at an accurate determination of body composition. The variables which are presently preferred for determining body composition are impedance magnitude (Z), length (L) of the segments, and the cross-sectional area (A) of the segments. One additional variable which may be included may be that of gender. From these variables, the composition of the body segment is calculated based upon a compartmental conductivity model of the segment.

In the determination of body composition, the present invention treats body segments as consisting of a series of parallel compartments, each differing in its electrical admittance characteristics. Those skilled in the art will appreciate that admittance is the reciprocal of impedance. The net admittance of a body segment is the sum of the admittances of each compartment in the body segment. As an example of this portion of the method of the present invention, a three compartment model of a body segment will be considered. While other numbers of compartments for each body segment can be used in accordance with the present invention, the preferred number of compartments is three and it will be used to demonstrate how to calculate the volume fraction of body fat in accordance with the present invention.

In the present invention, a body segment is modelled as consisting of three electrically parallel compartments:

1) lean conductive mass, with a specific impedance $\zeta_l$;
2) fat tissue, with a specific impedance $\zeta_f$; and
3) non-conductive tissue, such as the mineral component of bone, air in the lungs, and similar materials.

For each of the body segments, it is preferred to measure total impedance magnitude, Z, length, L, and circumference at one or more positions, from which the cross-sectional area of the body segment can be estimated as $A_T =$ circumference$^2/4\pi$ and the average segmental specific impedance estimated as $\zeta_a = A*Z/L$. The segmental volume fraction of body fat (SBF$_v$) is estimated from a function of the variables shown in Equation (6):

$$SBF_v = \text{function}(\zeta_a, A_T, \text{sex}) \quad (6)$$

Algebraic manipulation of the rules for conductors in parallel applied to this system yields equations in several forms, including Equations (7), (8), and (9):

$$SBF_v = K_1(L/A_T*Z) + K_2*(A_N(\text{sex})/A_T - 1) \quad (7)$$

$$SBF_v = [-50*(L/A_T*Z) + 30*(1-(\tfrac{1}{2})*\text{sex}) - /A_T + 0.7]*100 \quad (8)$$

$$SBF_v = K_1(1 - \zeta_l\zeta_a) + K_2*(A_N(\text{sex})/A_T) \quad (9)$$

In addition, it is within the scope of the present invention to use an empirical function of the form set forth in Equation (10):

$$SBF_V = C_1*\zeta_a + C_2(\text{sex})/A_t + C_3(\text{sex}) \quad (10)$$

where:
SBF$_v$ is fractional volume body fat;
$K_1 = (\zeta_f \zeta_l/(\zeta_l - \zeta_f))$;
$K_2 = K_1/\zeta_l$; and
$A_n$(sex) is a sex dependent expression of the non-conductive tissue cross-sectional area. As examples, this expression may be a (sex-dependent) constant, or a (sex-dependent) fixed proportion of $A_T$.

The coefficients (Cs, Ks) in these functions can be determined by obtaining data for tissue conductivities and bone volumes from various literature readily available in the art. Alternatively, the coefficients (Cs, Ks) in these functions can be determined by multiple linear regression techniques applied to data obtained from a representative sample population. Examples of illustrative coefficients which can be used in accordance with the present invention, but which are not intended to be limiting of the present invention can be calculated in accordance with Equation (8) and using the information set forth in FIGS. 6A and 6B discussed below.

Total body composition for a subject is determined from the variables obtained for a single segment or, preferably a combination of body segments, as shown in Equation (11) to arrive at total body fat (TBF$_v$).

$$TBF_v = C1*SBF_{trunk} + c2*SBF_{thigh} + c3*SBF_{upper\ arm} + C4(\text{sex}) \quad (11)$$

where:
c4 (sex) is a sex-dependent term to account for the contribution to lean body mass from the hands, feet, head, and other areas with body fat distribution different than in the region measured.

Body composition on a weight (mass) basis can be determined from the volume distributions calculated from the bioelectrical impedance analysis method in accordance with the present invention by adjusting for the differences in density between fat and lean body tissue. Doing this adjustment provides data comparable to that obtained, for instance, by hydrostatic weighing.

It will be understood that the method of the present invention can be carried out on an automated basis using an appropriately programmed microprocessor or may be carried out with a human manually obtaining all of the desired measurements and making the necessary calculations. Using the teachings contained herein, those skilled in the art can arrive at many different structures which can be used to carry out the method of the present invention.

Figure 5:
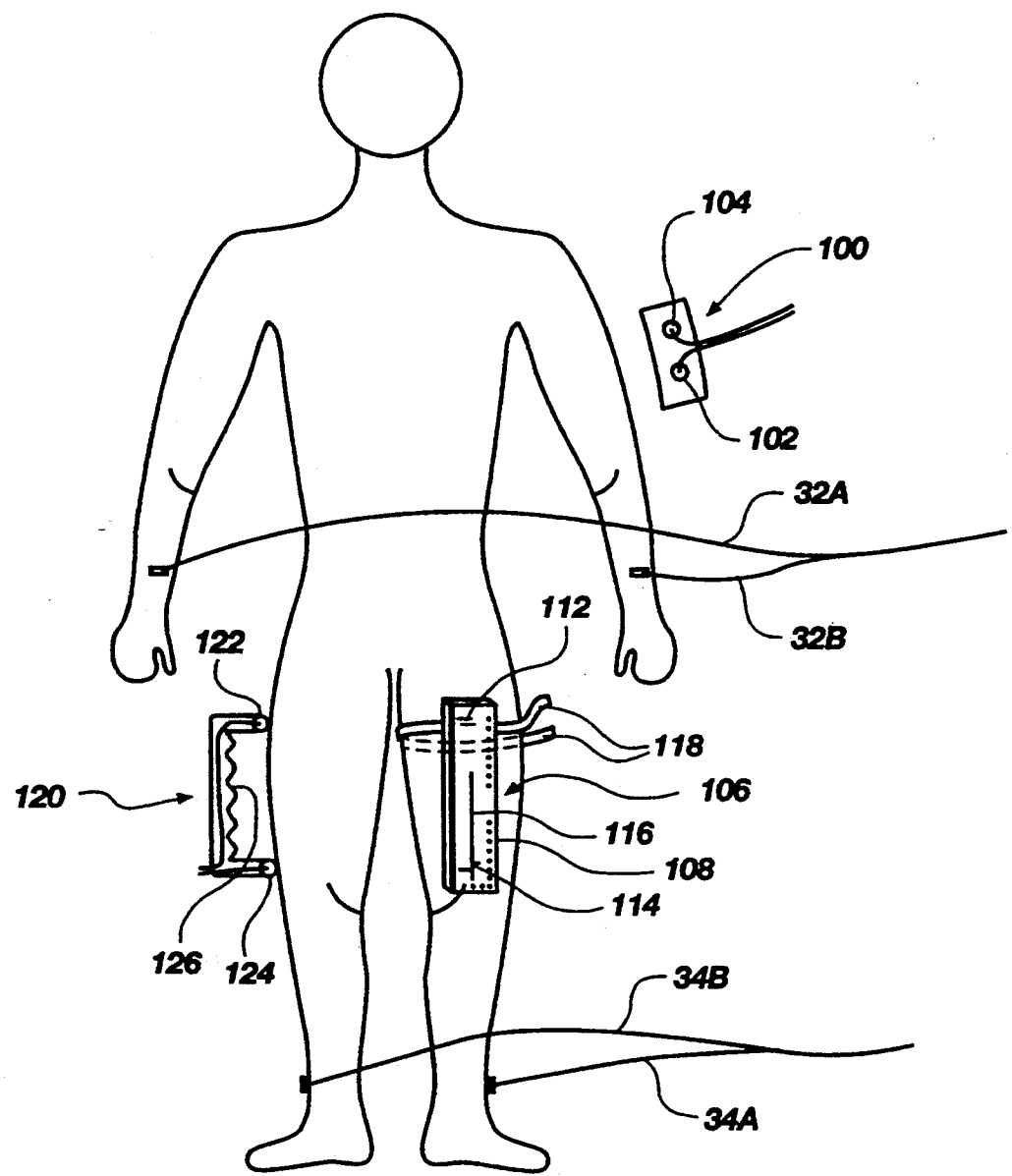
FIG. 5 is illustrates a plurality of devices used in accordance with the present invention.

In order facilitate carrying out the new method of the present invention, structures represented in FIG. 5 are provided. Since, in contrast to the prior bioelectrical body composition analysis techniques, the present invention requires that electrodes be placed on particular body segments, structures are provided to readily hold the electrodes in the proper positions.

As mentioned earlier, while many different types of electrodes can be used, it is preferred that the one of many commercially available EKG electrodes be used to provide the best results. It will be understood that the structures represented in FIG. 5 can use such EKG electrodes or other types of electrodes in accordance with the present invention.

Each of the electrode holder structures represented in FIG. 5 may be suited for use on a particular body segment or on a number of body segments. An adhesive membrane electrode holder 100 is illustrated in which two electrodes 102 and 104 are mounted. The adhesive membrane electrode holder may be particularly suited for body segments, such as the arm segment, where the distance between the electrodes is relatively short. In use, the distance between the electrodes 102 and 104 on the adhesive electrode holder 100 can be set and then the holder 100 placed on the body segment for impedance measurement and then repeatedly removed and placed on another location on the same segment until the measurements for that segment are completed.

Another electrode holder 106 shown in FIG. 5 includes a fixed electrode 112 and a movable electrode 114. Positioned within a housing 106 is a means 116 for adjusting the distance between the fixed electrode 112 and the movable electrode 114. A flexible measuring tape 118 is slidably attached to the housing 108 and can be used to obtain the circumference measurements of the body segment in accordance with the present invention. Once the fixed electrode 112 is in place, the movable electrode 114 can be positioned as desired. The measuring tape 118 can also be positioned and various circumference measurements obtained.

Also illustrated in FIG. 5 is an electrode holder 120 which includes two electrodes 122 and 124 which are spaced apart by a hand grip 126. It is to be understood that any electrode holder used in connection with the present invention should be configured to provide good electrical contact between the electrode and the subject's body. The branched leads 32A&B and 34A&B represented in FIG. 5 can be readily fabricated using materials available in the art.

EXAMPLE

The new method for determining body composition in accordance with the present invention was evaluated with thirty human subjects. The results obtained using the present invention were compared to results obtained using a prior bioelectrical body composition technique which is widely known (H. C. Lukaski, W. W. Bolonchuk, and W. A. Siders, "Validation of tetrapolar bioelectrical impedance method to assess human body composition," *J. Appl. Physiol.* 60:1327-32 (1986)). Hydrostatic weighing was used as the standard for comparison of both the results obtained by the prior technique and the results obtained by the present invention as described herein.

Figure 6A:
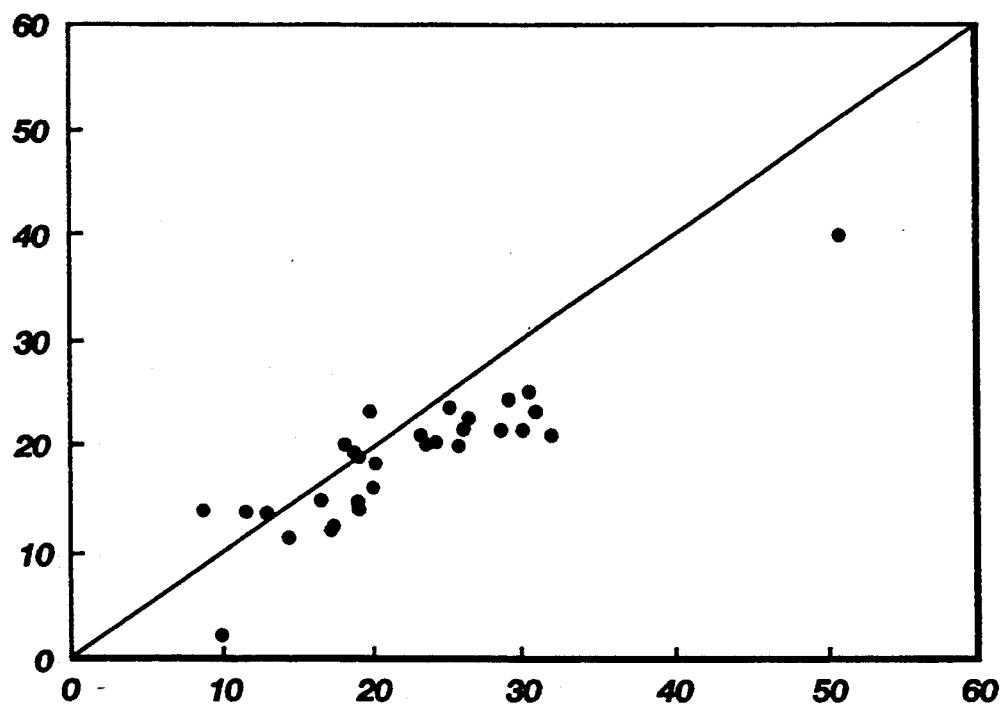
FIGS. 6A and 6B are charts showing the results of the present invention in comparison to a prior method.
Figure 6B:
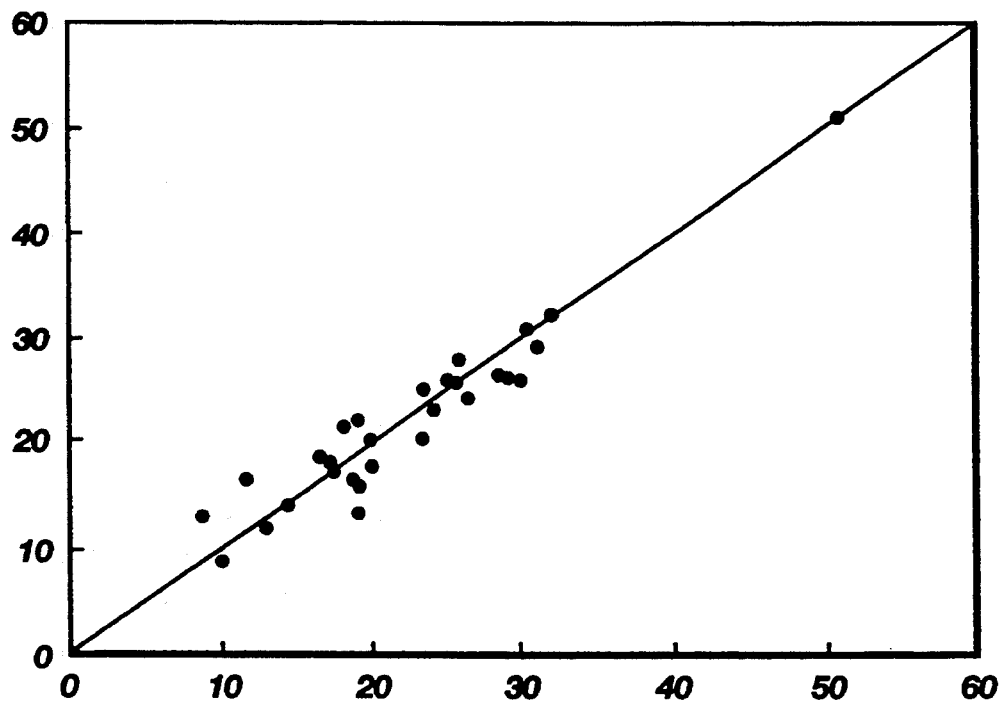

The results obtained using the prior method are represented in the graph of FIG. 6A. The results obtained using the method of the present invention are represented in the graph of FIG. 6B. In the graphs of FIGS. 6A and 6B, the horizontal axis represents the percentage of body fat determined using hydrostatic weighing, also referred to as hydrodensitometry, while the vertical axis represents the percentage of body fat determined using the respective bioelectrical impedance method. The equations used to obtain the data set forth in FIG. 6B are provided below as Equations (12), (13), (14), and (15):

$$SBF_{trunk} = 0.0889 * \zeta_a - (3039 + 2136 * sex) / A_T + 10.963 \quad (12)$$

$$SBF_{thigh} = 0.0851 * \zeta_a - (2589 + 999 * sex) / A_T + 22.893 \quad (13)$$

$$SBF_{upperarm} = 0.0862 * \zeta_a - (605.4 + 260.4 * sex) / A_T + 16.658 \quad (14)$$

where,
$A_T$ = cross-section area of body segment (cm²)
sex = 1 for male & 0 for female $$TBF = 0.362 * SBF_{trunk} + 0.945 * SBF_{thigh} - 0.303 * SBF_{upperarm} \quad (15)$$

The use of the prior method gave a square correlation coefficient ($r^2$) of 0.801 and a standard error of estimation (SEE) OF 3.71%. The method of the present invention, using Equations (10) and (11), gave an $r^2$ of 0.914 and a SEE of 2.58%. Comparison of the graphs of FIGS. 6A and 6B shows the much better results obtained with the present invention.

In view of the foregoing, it will be appreciated that the present invention provides an improved method and apparatus for measuring body composition by bioelectrical impedance and which accounts for differences between various subjects which caused inaccuracies in prior techniques. The present invention also provides a method and apparatus for measuring body composition which is more accurate and more convenient than other widely accepted methods of determining body composition.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method of determining the body composition of a subject comprising the steps of:
   selecting a first body segment, the first body segment comprising substantially less than the whole body of the subject, and determining the characteristics of the first body segment utilizing a method comprising the steps of:
      causing a current flow through the first body segment;
      measuring the impedance to the current flow of the first body segment;
   selecting a second body segment, the second body segment comprising substantially less than the whole body of the subject, and determining the characteristics of the second body segment utilizing a method comprising the steps of:
      causing a current flow through the second body segment;
      measuring the impedance to the current flow of the second body segment; and
   determining the total body composition in accordance with measured impedance of the first body segment and the measured impedance of the second body segment.

2. A method of determining body composition as defined in claim 1 wherein the first body segment is chosen from a group consisting of the thigh, truck, and upper arm of the subject.

3. A method of determining body composition as defined in claim 1 further comprising measuring the length of the first body segment and the circumference of the first body segment and calculating a first body segment cross sectional area and wherein the step of determining the characteristics of the first body segment further comprises the step of determining the composition of the first body segment from the impedance derived from a voltage sensed at a first location and a second location on the subject's body in combination with the measured length of the first body segment and the cross sectional area of the first body segment.

4. A method of determining body composition as defined in claim 3 wherein the step of measuring the circumference of the first body segment comprises the step of obtaining a plurality of circumference measurements each at a different location along the length of the first body segment.

5. A method of determining body composition as defined in claim 1 further comprising the step of determining the gender of the subject and wherein the step of determining the characteristics of the first body segment further comprises the step of considering the subject's gender to determine the composition of at least the first body segment.

6. A method of determining body composition as defined in claim 1 wherein the step of determining the characteristics of the first body segment comprises the step of applying an equation of the form:

$$SBF_v = C_1 * F(\zeta_a) + C_2(sex)/A_T + C_3(sex)$$

wherein:
SBF$_v$ is segmental body fat on a volume fraction basis,
F($\zeta_a$) is the segmental specific impedance or its inverse,
A$_T$ is segmental average cross-sectional area,
(sex) indicates a gender dependent constant, and the coefficients of the variables are determined from empirical data collection.

7. A method of determining body composition as defined in claim 1 wherein the subject comprises four extremities and wherein the step of causing a current flow through the first body segment and wherein the step of causing a current flow through the second body segment together comprise the step of attaching an electrode to the distal portion of each of the subject's extremities.

8. A method of determining body composition as defined in claim 1 wherein the step of measuring the impedance to the current flow of the first body segment comprises the step of attaching a first electrode at a first end of the first body segment and measuring the voltage thereat and the step of attaching a second at a second end of the first body segment and measuring the voltage thereat.

9. A method of determining body composition as defined in claim 1 further comprising the step of determining the gender of the subject and wherein the step of determining the characteristics of the first body segment further comprises the step of considering the subject's gender to determine the first body segment's composition.

10. A method of determining body composition as defined in claim 1 further comprising the step of estimating the composition of the entire subject's body.

11. A method of determining body composition as defined in claim 1 wherein the body composition material is one selected from a group consisting of fat, lean body mass, total body water, inter-cellular fluid, and extra-cellular fluid.

12. A method of determining body composition as defined in claim 1 further comprising the steps of:
selecting a third body segment, the third body segment comprising substantially less than the whole body of the subject and determining the characteristics of the third body segment utilizing a method comprising the steps of:
causing a current flow through the third body segment; and
measuring the impedance to the current flow of the third body segment.

13. A method of determining the body composition of a subject, the subject having four extremities, the method comprising the steps of:
injecting a current into a distal portion of a first extremity of the subject's body;
injecting a current into a distal portion of a second extremity of the subject's body simultaneously with that injected into the first extremity;
injecting a current into a distal portion of a third extremity of the subject's body simultaneously with that injected into the first and second extremities;
injecting a current into a distal portion of a fourth extremity of the subject's body simultaneously with that injected into the first, second, and third extremities;
selecting a first body segment, the first body segment comprising substantially less than the whole body of the subject;
sensing the voltage at a first location on the first body segment;
sensing the voltage at a second location on the first body segment to arrive at the bioelectrical impedance of the first body segment, the second location on the first body segment being spaced apart from the first location on the first body segment;
selecting a second body segment, the second body segment comprising substantially less than the whole body of the subject;
sensing the voltage at a first location on the second body segment;
sensing the voltage at a second location on the second body segment to arrive at the bioelectrical impedance of the second body segment, the second location on the second body segment being spaced apart from the first location on the second body segment; and
determining the composition of the subject's body using the voltages sensed at the first body segment and the second body segment of the subject's body.

14. A method of determining the body composition of a subject as defined in claim 13 wherein the first body segment is one chosen from a group consisting of the thigh, truck, and upper arm segments of the subject.

15. A method of determining the body composition of a subject as defined in claim 13 further comprising the steps of measuring the length of the first body segment and measuring the circumference of the first body segment and calculating a first body segment cross sectional area and wherein the step of determining the composition of the subject's body further comprises the step of determining the composition of the first body segment from the bioelectrical impedance derived from the voltage sensed at the first location and at the second location on the first body segment of the subject's body in combination with the measured length of the first body segment and the cross sectional area of the first body segment.

16. A method of determining the body composition of a subject as defined in claim 15 further comprising the steps of determining the gender of the subject and the step of determining the composition of the subject's body further comprises the step of considering the subject's gender to determine the composition of subject's body.

17. A method of determining the body composition of a subject as defined in claim 13 wherein the step of determining the composition of the subject's body comprises the step of determining the composition of the first body segment by applying an equation of the form:

$$SBF_v = C_i * F(\zeta_a) + C_2(\text{sex})/A_T + C_3(\text{sex})$$

where

SBF$_v$ is segmental body fat on a volume fraction basis, $F(\zeta_a)$ is the segmental specific impedance or its inverse, $A_T$ is segmental average cross-sectional area, (sex) indicates a gender dependent constant, and the coefficients of the variables are determined from empirical data collection.

18. A method of determining the body composition of a subject as defined in claim 13 wherein the body composition material is one selected from a group consisting of fat, lean body mass, total body water, inter-cellular fluid, and extra-cellular fluid.

19. A method of determining the amount of fat contained in at least a portion of the body of a subject, the subject having two arms and two legs, the method comprising the steps of:
attaching a first electrode to a distal portion of the subject's first arm;
providing a current to the first electrode;
attaching a second electrode to a distal portion of the subject's second arm;
providing a current to the second electrode;
attaching a third electrode to a distal portion of the subject's first leg;
providing a current to the third electrode;
attaching a fourth electrode to a distal portion of the subject's second leg;
providing a current to the fourth electrode;
selecting a first body segment, the first body segment comprising substantially less than the whole body of the subject;
attaching a fifth electrode to a first end of the first body segment;
attaching a sixth electrode to a second end of the first body segment;
measuring the voltage difference between the fifth electrode and the sixth electrode to determine the bioelectrical impedance of the first body segment;
measuring the distance between the fifth electrode and the sixth electrode;
measuring the circumference of the first body segment; and
calculating the amount of fat in the first body segment based upon the voltage difference and the distance between the fifth and sixth electrodes and the diameter of the first body segment.

20. A method of determining the amount of fat contained in at least a portion of the body of a subject as defined in claim 19 wherein the first body segment is one chosen from a group consisting of the thigh, truck, and upper arm segments of the subject.

21. A method of determining the amount of fat contained in at least a portion of the body of a subject as defined in claim 19 further comprising the steps of
moving the fifth electrode to a first end of a second body segment;
moving the sixth electrode to a second end of a second body segment;
measuring the voltage difference between the fifth electrode and the sixth electrode to determine the bioelectrical impedance of the second body segment;
measuring the distance between the fifth electrode and the sixth electrode on the second body segment;
measuring the circumference of the second body segment; and
calculating the amount of fat in the second body segment based upon the voltage difference and the distance between the fifth and sixth electrodes and the diameter of the second body segment.

22. A method of determining the amount of fat contained in at least a portion of the body of a subject as defined in claim 19 further comprising the step of determining the gender of the subject and wherein the step of calculating the amount of fat in the first body segment further comprises the step of considering the subject's gender to determine the composition of the first body segment.

23. A method of determining the amount of fat contained in at least a portion of the body of a subject as defined in claim 19 wherein the step of calculating the amount of fat in the first body segment comprises the step of calculating the amount of fat in the first body segment by applying an equation of the form:

$$SBF_v = C_i * F(\zeta_a) + C_2(\text{sex})/A_T + C_3(\text{sex})$$

where

SBF$_v$ is segmental body fat on a volume fraction basis, $F(\zeta_a)$ is the segmental specific impedance or its inverse, $A_T$ is segmental average cross-sectional area, (sex) indicates a gender dependent constant, and the coefficients of the variables are determined from empirical data collection.

24. A method of determining the amount of fat contained in at least a portion of the body of a subject as defined in claim 19 further comprising the step of calculating the amount of material in the first body segment wherein the material is one selected from a group consisting of lean body mass, total body water, intra-cellular fluid, and extra-cellular fluid.

25. A method of determining the body composition of at least a portion of a subject, the subject having four extremities, the method comprising the steps of:
injecting a current into a distal portion of a first extremity of the subject's body;
injecting a current into a distal portion of a second extremity of the subject's body simultaneously with that injected into the first extremity;
injecting a current into a distal portion of a third extremity of the subject's body simultaneously with that injected into the first and second extremities;
injecting a current into a distal portion of a fourth extremity of the subject's body simultaneously with that injected into the first, second, and third extremities;
selecting a first body segment, the first body segment comprising substantially less than the whole body of the subject.
sensing the voltage at a first location on the first body segment;
sensing the voltage at a second location on the first body segment, the second location being spaced apart from the first location; and
determining the composition of at least the first body segment from an impedance derived from the voltage sensed at the first location and the second location of the subject's body.

26. An apparatus for determining the bioelectrical impedance of at least a portion of a subject having four extremities, the apparatus comprising:
  current means for generating a current;
  means for injecting the current into a distal portion of a first extremity of the subject's body;
  means for injecting the current into a distal portion of a second extremity of the subject's body;
  means for injecting the current into a distal portion of a third extremity of the subject's body;
  means for injecting the current into a distal portion of a fourth extremity of the subject's body;
  voltage means for measuring voltage found on the subject's body;
  means for sensing a first voltage present at a first location on the subject's body and conveying the first voltage to the voltage means;
  means for sensing second voltage present at a second location on the subject's body, the second location being spaced apart from the first location, and conveying the second voltage to the voltage means; and
  means for outputting an impedance of the subject's body between the means for sensing a first voltage and the means for sensing a second voltage.

27. An apparatus for determining the bioelectrical impedance of at least a portion of a subject as defined in claim 26 wherein the first location is one end of a body segment and the second location is the opposite end of the body segment wherein the body segment is one selected from a group consisting of a thigh segment, a truck segment, and an upper arm segment of the subject.

28. An apparatus for determining the bioelectrical impedance of at least a portion of a subject as defined in claim 26 wherein the means for injecting the current into a distal portion of a first extremity and the means for injecting the current into a distal portion of a second extremity comprises a pair of electrodes each connected in parallel and connected to a constant current source.

* * * * *